United States Patent [19]
Hull et al.

[11] Patent Number: 5,056,532
[45] Date of Patent: Oct. 15, 1991

[54] ESOPHAGEAL PACING LEAD

[75] Inventors: Vincent Hull, Fridley; Creg Dance, Elk River; Terrell Williams, Coon Rapids; Wayne Voightschild, Apple Valley, all of Minn.

[73] Assignee: Medtronic, Inc., Minneapolis, Minn.

[21] Appl. No.: 385,348

[22] Filed: Jul. 25, 1989

[51] Int. Cl.⁵ ............................................. A61N 1/00
[52] U.S. Cl. .................................... 128/785; 128/715; 128/419 D
[58] Field of Search ............... 128/785, 784, 786, 642, 128/715, 419 D

[56] References Cited

U.S. PATENT DOCUMENTS 4,198,963 4/1980 Barkalow et al. ..................... 128/53
4,574,807 3/1986 Hewson et al. .............. 128/419 PG
4,706,688 11/1987 Michael et al. ...................... 128/785

Primary Examiner—William E. Kamm
Assistant Examiner—Scott R. Akers

[57] ABSTRACT

An electrical lead having an elongated flexible lead body having a flattened cross sectional configuration. One flattened surface is provided with at least one aperture open to a longitudinal lumen carrying an electrode lead. The electrode lead is provided with electrodes located within the aperture, and the electrode lead is slideable within the lead body to allow for adjustment of the position of the electrodes within the aperture. The lead body is also provided with at least one expansible balloon, located radially opposite the aperture. In use, the lead is advanced down the esophagus, with the surface of the lead bearing the aperture facing anteriorly. Inflation of the balloon urges the aperture and the electrodes located therein adjacent the anterior surface of the esophagus. After inflation of the balloon, the electrode lead may be moved within the lead body to allow for adjacent of electrode location.

10 Claims, 5 Drawing Sheets

ESOPHAGEAL PACING LEAD

BACKGROUND OF THE INVENTION

The present invention relates to the field of medical electrical leads generally, and more specifically to esophageal stimulation and monitoring leads.

Esophageal stimulation and monitoring leads are known to the art. These include leads adapted specifically for cardiac pacing, such as disclosed in U.S. Pat. No. 4,574,807 issued to Hewson et al and leads adapted for use in pacing, EKG monitoring and defibrillation, as disclosed in U.S. Pat. No. 4,198,936 issued to Barkalow et al and U.S. Pat. No. 4,706,688 issued to Michael et al.

Typically, esophageal pacing leads include one or more balloons, adapted to stabilize the location of the lead in the esophagus. In some cases, the electrodes are located on the balloon, as in the above cited Barkalow et al patent. In other cases, the electrodes are located proximal or distal to the balloon as illustrated in the above-cited Hewson et al patent. In some cases, the balloon is arranged eccentrically, and is used both to stabilize the lead and urge the electrodes into contact with the anterior inner surface of the esophagus, which is closest to the heart. Such a configuration is illustrated in the above cited Michael et al patent.

SUMMARY OF THE INVENTION

With the esophageal leads discussed above, adjustment of the electrodes after initial inflation of the balloon requires deflation of the balloon and movement of the entire lead. The present invention provides a more convenient method of adjusting the location of the electrodes. In its preferred embodiment, the esophageal lead of the present invention is provided with atrial and ventricular electrodes, intended to be located near the atria and the ventricles of the heart. The electrodes are mounted on an electrode lead slideably mounted within a lumen of the esophageal lead body. The esophageal lead body is provided with apertures in the vicinity of the atrial and ventricular electrodes and extending linearily along the esophageal lead body for a distance greater than the lineal length of the atrial and ventricular electrodes. This allows movement of the electrode lead relative to the esophageal lead, and thereby allows adjustment of electrode location after the esophageal lead has been stabilized.

An additional feature of the invention is the flattened cross section of the esophageal lead body which assists in locating the electrode lead adjacent the anterior inner surface of the esophagus. The lead body displays two flattened surfaces opposite one another and rounded edge surfaces. The lead body therefore bends more easily in the plane perpendicular to the flattened surfaces. The apertures associated with the atrial and ventricular electrodes are located on the lower surface of the esophageal lead body. When inserted, the lead passes back through the oral or nasal cavity and then bends downward to follow the esophagus, the distal end of the lead being placed in the stomach, adjacent the gastroesophageal junction. Maintaining the lower surface of the esophageal lead adjacent facing downward as it enters the oral or nasal passage assures that the electrodes will be facing the anterior inner surface of the esophagus, as close as possible to the heart.

DETAILED DESCRIPTION OF THE INVENTION

Figure 1:
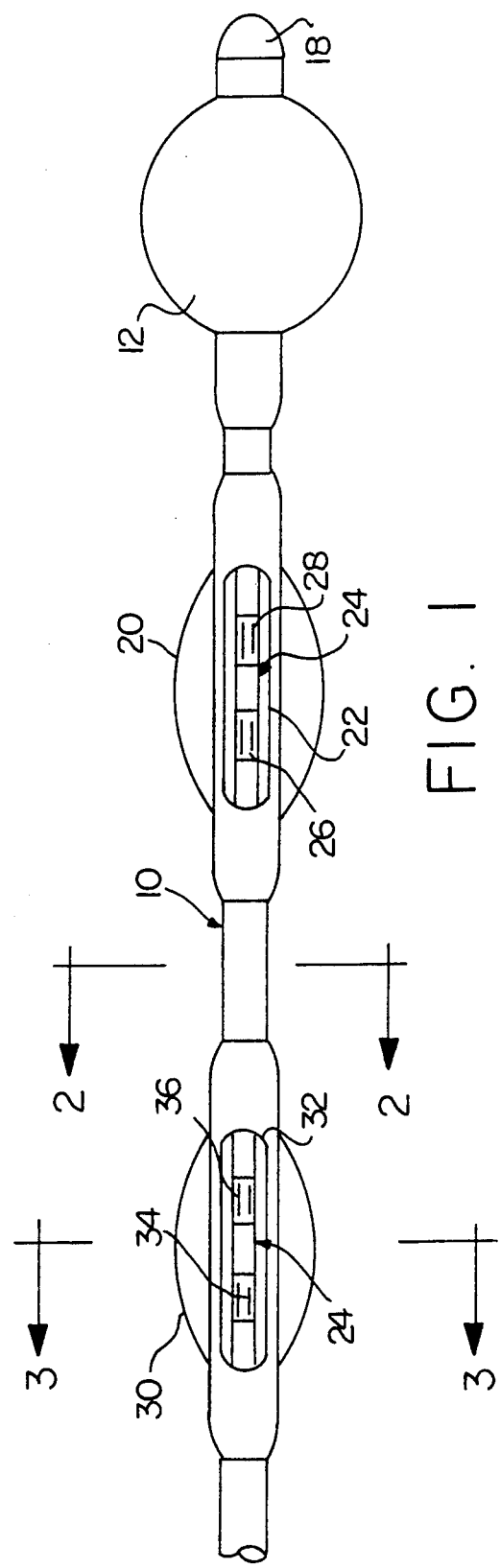
FIG. 1 is a plan view of the lower surface of the distal portion of the lead according to the present invention.

FIG. 1 shows a plan view of the lower surface of the distal end of an esophageal lead according to the present invention. The lead comprises an elongated flexible lead body 10, which is provided with three longitudinal lumens. The lead is flattened in cross section, with the thickness of the lead being substantially less than the width of the lead as seen in this view. Lead body 10 may be provided with depth markings (not illustrated) to assist the physician in determining the degree of insertion of the lead. At the distal end of the lead a balloon 12 is mounted around the external surface of the lead body 10. Lead body 10 and balloon 12 may both be fabricated of silicone rubber. Balloon 12 may be adhesively coupled to or molded to lead body 10. The interior of balloon 12 is in fluid communication with one of the three lumens running through lead body 10. To facilitate passage of the lead down the esophagus, a rounded silicone rubber tip 18 is provided at the distal extremity of lead body 10.

Proximal to balloon 12 is a second balloon 20, which is adhesively bonded to or molded to lead body 10. The interior of balloon 20 is open to a second balloon inflation lumen, not visible in this view. Opposite balloon 20, the lower surface 11 of lead body 10 is cut back to form an aperture 22 through which electrode lead 24 is visible. Electrode lead 24 is slideably mounted within a third lumen within lead body 10. Ventricular electrodes 26 and 28, mounted to lead 24, are visible through aperture 22 which is open to the third lumen within lead body 10. Because lead 24 is slideable within the lumen of the esophageal lead, the positions of electrodes 26 and 28 may be adjusted relative to the position of balloon 20.

A third balloon 30 is located proximal to balloon 20, and is adhesively bonded to or molded to the body 10. The interior of balloon 30 is also open to the second lumen through the lead body. Opposite balloon 30 is a second aperture 32 through which a more proximal portion of lead 24 is visible. Atrial electrodes 34 and 36 are located on electrode lead 24, aligned with aperture 32. Movement of lead 24 within the lead body 10 also adjusts the positions of electrodes 34 and 36 relative to balloon 30. Electrode lead 24 should extend distally from electrode 28 a distance sufficient to retain the distal end of lead 24 in the third lumen when electrodes 26 and 28 are in their most proximal location with respect to aperture 22.

Balloons 20 and 30 are preferably fabricated of silicone rubber or other elastic material, allowing for expansion of the balloon during inflation. Preferably, balloons 20 and 30 are "floppy" balloons, which when deflated do not lie tightly against the outer surface of lead body 10. This structural feature reduces the amount of elastic stretching required to inflate the balloons, and assists in allowing the lead body 10 to maintain a linear configuration after inflation of the balloons.

In use, it is anticipated that electrodes 26 and 28 will be placed roughly adjacent the ventricles of the heart, with electrodes 34 and 36 placed roughly adjacent the atria of the heart. Balloon 12 will be located within the stomach, adjacent the point at which the esophagus enters the stomach. To facilitate location of electrodes 26 and 28 adjacent the ventricles of the heart, the center of aperture 22 is located about 3 cm proximal to the proximal end of balloon 12. To facilitate location of electrodes 34 and 36 adjacent the atrium of the heart, the center of aperture 32 is located about 9 cm proximal to the proximal end of balloon 12.

The lead is inserted into the mouth or nose with the lower surface 11 of lead body 10 facing downward. The lead is advanced through the mouth or the nasal cavity, down the esophagus until the distal end 18 of the lead is well within the stomach. At this point, balloon 12 is inflated, and the lead is withdrawn until balloon 12 lies against the gastroesophageal junction. Balloons 20 and 30 are then inflated, urging electrode lead 24 against the anterior inner surface of the esophagus, closest to the heart. This stabilizes the location of the esophageal lead. After inflation of balloons 20 and 30, electrode lead 24 may be moved proximally and distally while connected to monitoring equipment to optimize the location for EKG monitoring. The location of the lead 24 may also be adjusted to produce minimum pacing thresholds.

As configured, the lead is optimized for A-V sequential pacing. However, leads employing only a single balloon and a single aperture would also be useful in the context of single chamber pacing. An alternative design for an A-V lead might employ a single elongated balloon, substituting for balloons 20 and 30. An additional alternative would be to employ a single elongated aperature as a substitute for both apertures 22 and 32, through which both the atrial and ventricular electrodes would be visible.

Figure 2:
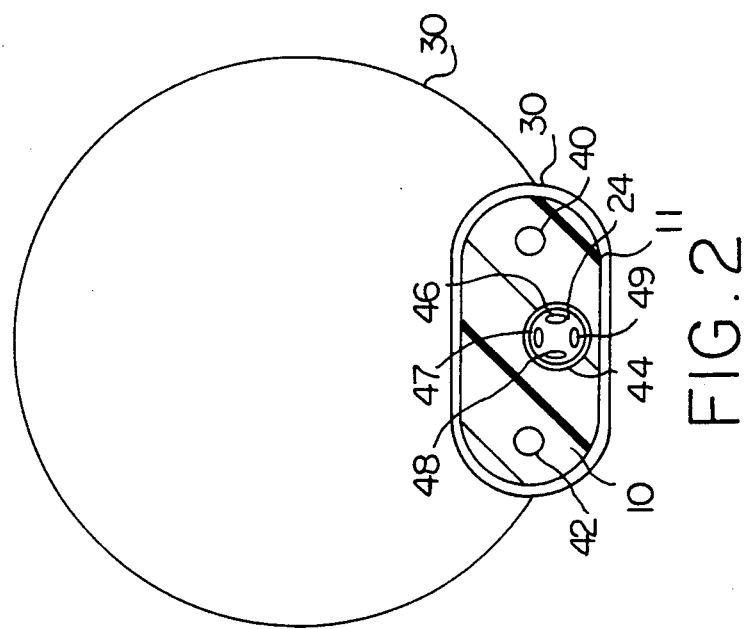
FIG. 2 is a cross sectional view through the lead of the present invention.

FIG. 2 shows a cross sectional view of the esophageal lead in the area between balloons 20 and 30, illustrating the flattened shape of the lead body 10, and the location of the first lumen 40, the second lumen 42 and the third lumen 44. Lead 24 is seen in cross section in lumen 44. As illustrated, lead 24 contains four elongated conductors 46, 47, 48 and 49, which are coupled to electrodes 26, 28, 34 and 36, respectively. Electrode lead 24 may be any multiple electrode lead of appropriate diameter, provided that the electrodes located thereon have appropriate interelectrode spacing to correspond to the location of apertures 22 and 32 (FIG. 1).

Figure 3:
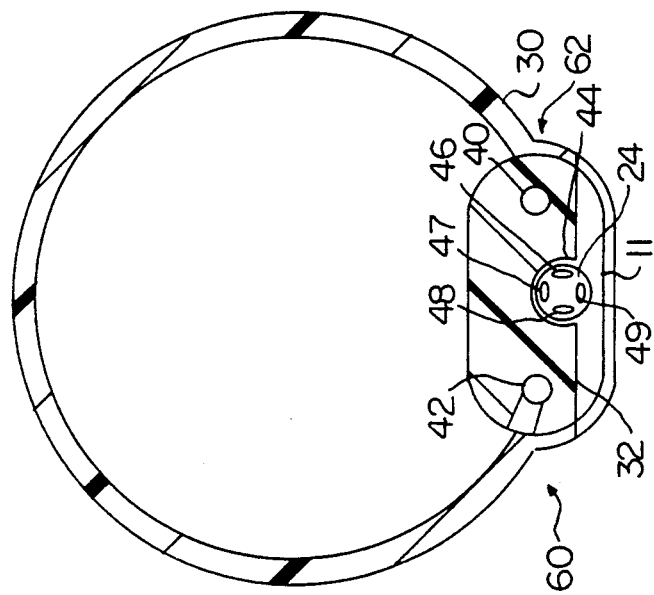
FIG. 3 is a second cross sectional view through the lead of the present invention.

FIG. 3 is a cross sectional view of the esophageal lead taken through balloon 30. In this view, the cross sectional configuration of aperture 32 is visible. Balloon 30, shown in its inflated configuration, is adhesively bonded or molded to lead body 10, around the periphery of aperture 32. Lead 24 is visible within third lumen 44.

When inflated, balloon 30 is expanded against the posterior inner surface of the esophagus, urging electrodes 34 and 36 (FIG. 1) into contact with the anterior inner surface of the esophagus. It should be noted that when inflated, the outer surfaces of balloon 30 and lead body 10, taken in cross section define two notches 60 and 62. Balloon 20 (FIG. 1) and lead body 10 also display the same configuration when balloon 20 is inflated. This structure, like that illustrated in the above cited Michael et al patent, allows for passage of fluid down the esophagus, past the balloons, if desired.

Figure 4:
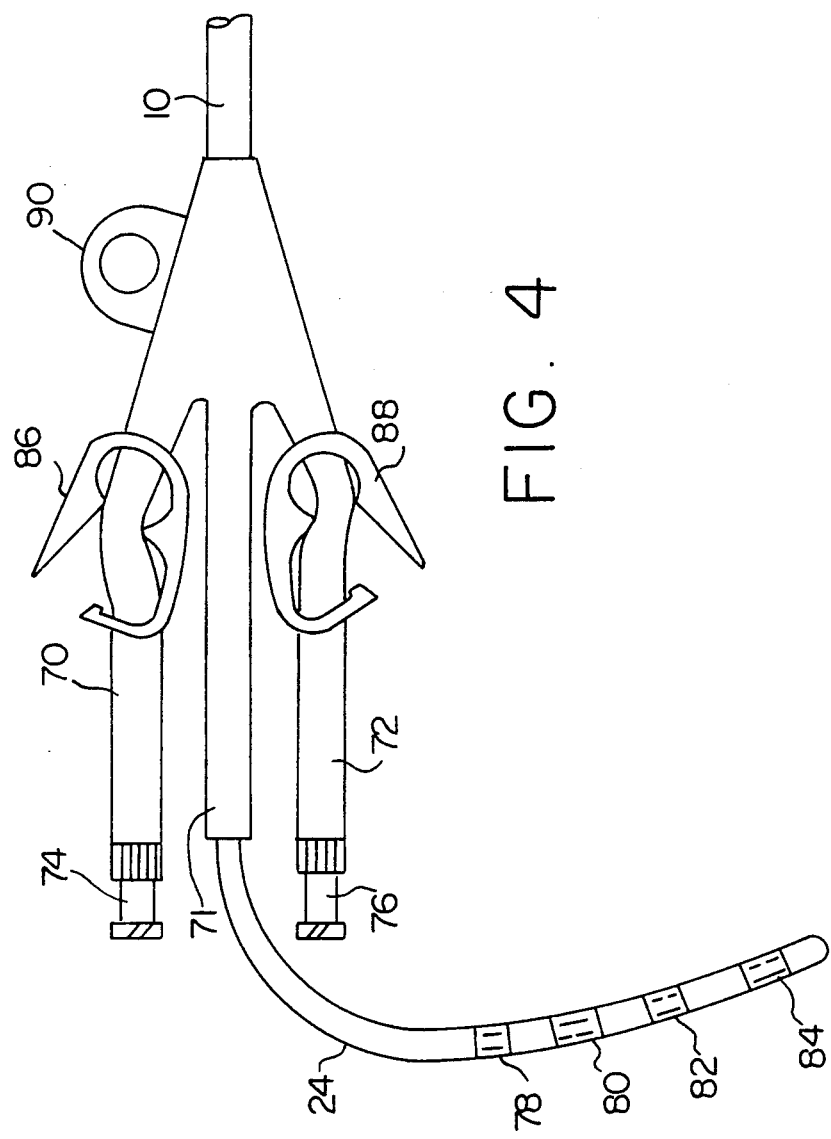
FIG. 4 is a side plan view of the proximal end of a lead according to the present invention.

FIG. 4 is a side plan view of the proximal end of a lead according to the present invention. Extending from the proximal end of lead body 10 are three elongated tubes 70, 71 and 72 coupled to lumens 40, 44, and 42, respectively. At the proximal ends of tubes 70 and 72 are luer locks 74 and 76, respectively, allowing the coupling of a syringe for inflation and deflation of the balloons located on the lead. Tubing clips 86 and 88 may be used to clamp tubes 70 and 72 after inflation of the balloons. Extending from the proximal end of lead body 10 is electrode lead 24. The proximal end of electrode lead 24 bears four electrical connector surfaces 78, 80, 82 and 84, each of which is coupled to one of electrodes 26, 28, 34 and 36 by means of one of conductors 46, 47, 48 and 49. Connectors 78, 80, 82 and 84 in use will be coupled to EKG monitoring and/or electrical stimulation apparatus. A molded flange or ring 90 allows the proximal end of the lead body 10 to be secured to prevent movement of the lead in a proximal direction after insertion into the esophagus.

Figure 5:
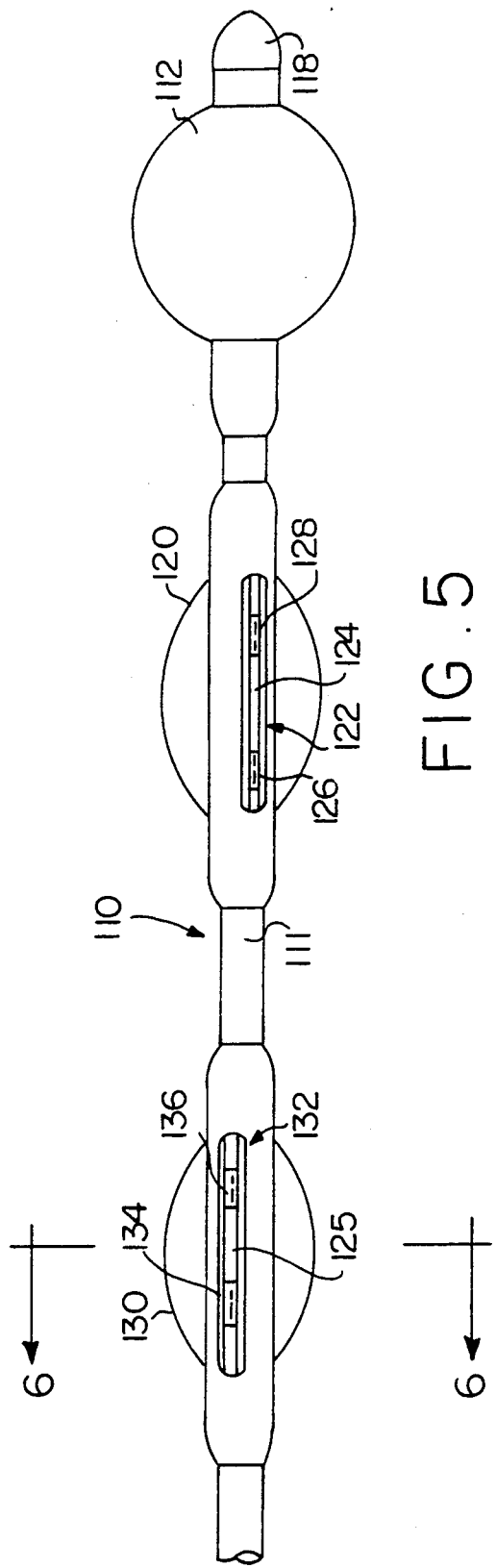
FIG. 5 is a plan view of the lower surface of a second embodiment of a lead according to the present invention.

FIG. 5 is a side plan view of a second embodiment of an esophageal lead according to the present invention. The lead comprises an elongated flexible lead body 110 which is provided with four longitudinal lumens. The lead is flattened in cross section, with the thickness of the lead being substantially less than the width of the lead as seen in this view. The distal end of the lead is provided with a balloon 112, mounted around the external surface of lead body 110. The interior of balloon 112 is in fluid communication with one of the four lumens running through the body 110. To facilitate passage of the lead down the esophagous, a rounded silicone rubber tip 118 is provided at the distal extremity of lead body 110.

Proximal to balloon 112 is a second balloon 120 which is adhesively bonded to or molded to lead body 110. The interior of balloon 120 is open to a second one of the four lumens running through lead body 110. Opposite balloon 120, the lower surface 111 of lead body 110 is cut back to form an aperture 122 through which electrode lead 124 is visible. Electrode lead 124 is slideably mounted within a third lumen within lead body 110. Ventricular electrodes 126 and 128, mounted to lead 124, are visible through aperture 122 which is open to the third lumen within lead body 110. Because lead 124 is slideable within the third lumen of the esophageal lead, the positions of electrodes 126 and 128 may be adjusted relative to the position of balloon 20.

A third balloon 130 is located proximal to balloon 120. Opposite balloon 130 is a second aperture 132 through which electrode lead 125 is visible. Electrode head 125 is slideably mounted with the fourth lumen within lead body 110. Atrial electrodes 134 and 136 are located on electrode lead 125, aligned with aperture 132. Movement of lead 125 within lead body 110 adjusts the positions of electrodes 134 and 136 relative to balloon 30.

Electrode leads 124 and 125 should both extend distally from their electrodes a distance sufficient to retain the distal ends of leads 124 and 125 within their respective lumens when the electrodes they carry are in their most proximal location within apertures 122 and 132. In this embodiment, the relative positions of the atrial and ventricular electrodes can be adjusted, allowing for more precise localization of sensing and pacing functions than would be possible with the lead illustrated in FIG. 1, in which the distance between the atrial and ventricular electrodes is fixed.

Figure 6:
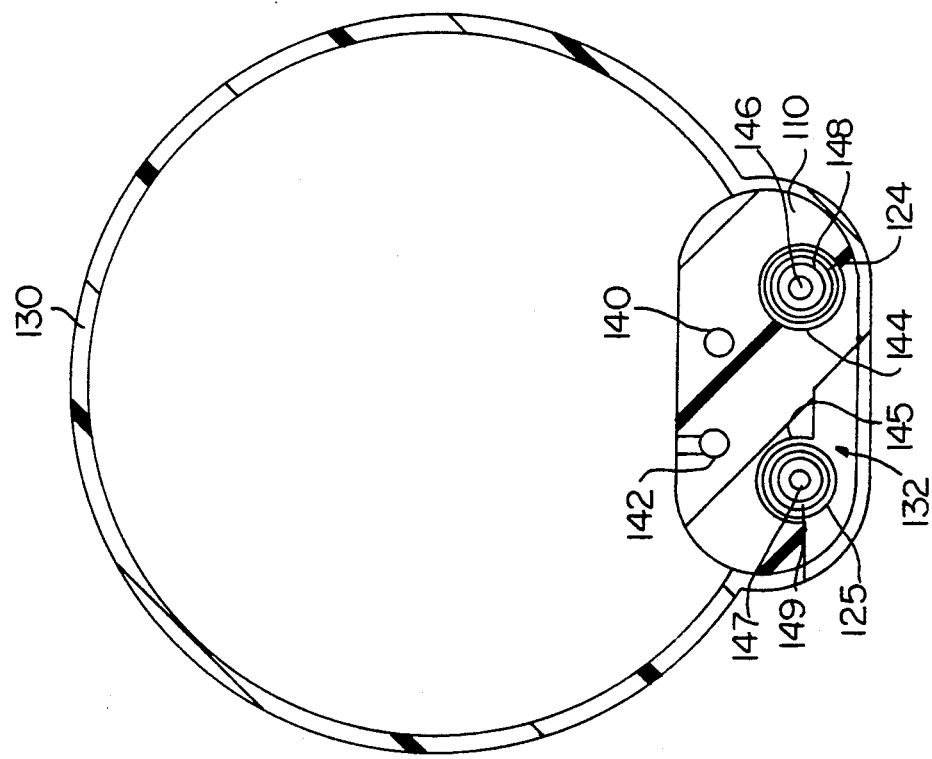
FIG. 6 is a cross sectional view through a second embodiment of a lead according to the present invention.

FIG. 6 is a cross sectional view of the esophageal lead of FIG. 5, taken through balloon 130. In this view, the cross sectional configuration of aperture 132, electrode leads 124 and 125, and lumens 140, 142, 144 and 145 are all visible. Balloon 130, shown in its inflated configuration is adhesively bonded or molded to lead body 110 around the periphery of aperture 132. Leads 124 and 125 are both illustrated as bipolar, coaxial leads, including outer conductors 146, 147 and inner conductors 148, 149. As in the case of the esophageal lead illustrated in FIGS. 1-3, electrode leads 124 and 125 may take the form of any commercially available electrode lead of appropriate diameter and length.

While the above embodiments employ balloons which when inflated urge the electrodes against the anterior inner surface of the esophagus, other expandable means for urging the electrodes into contact with the anterior inner surface of the esophagus are believed to be within the scope of the invention. For example, the balloons could be replaced with metallic or plastic prongs which would be in a closed position during the introduction of the lead, and expanded after introduction of the lead. Similarly, while the disclosed embodiments employ bipolar electrodes intended for use in the vicinity of the atrium and ventricle, configurations employing greater or lesser numbers of electrodes are also believed within the scope of the present invention. As such, the above disclosed embodiments should be considered exemplary, rather than limited with regard to the following claims.

In conjunction with the above disclosure, we claim:

1. A medical electrical lead comprising:
    an elongated flexible lead body having an outer surface, and having an elongated lead lumen;
    an electrode lead, slideably mounted within said elongated lead lumen, said electrode lead including at least one electrode;
    wherein said elongated lead body is provided with an elongated aperture, opening said lead lumen to the exterior surface of said lead body, said at least one electrode on said electrode lead located exposed to the exterior of said lead body within said elongated aperture, said lead body further comprising expondable means located radially opposite said aperture, and expandable in a direction opposite said aperture.

2. A medical lead according to claim 1 wherein said expandable means comprises at least one inflatable balloon, and wherein said lead body further comprises a first inflation lumen and a second aperture, opening said first inflation lumen to the interior of said balloon.

3. A medical lead according to claim 1 or claim 2 wherein said lead body further comprises an inflatable balloon located distal to said aperture, and further comprises a second inflation lumen in fluid communication with said distal balloon.

4. A medical lead according to claim 1 or claim 2 wherein said lead body in cross section displays a flattened configuration, having a flattened upper surface and a flattened lower surface opposite said upper surface, said first aperture located in said flattened lower surface.

5. A medical lead according to claim 4 wherein said expansible means is located on said upper surface.

6. A medical lead according to claim 1 wherein said expandable means comprises at least two spaced inflatable balloons and wherein said lead body comprises inflation lumen means for inflating said at least two balloons and wherein said lead body is provided with at least first and second elongated apertures, opening said lead lumen to the exterior surface of said lead body, one of said apertures located opposite one of said at least two balloons, the other of said apertures located opposite the other of said at least two balloons, and wherein said electrode lead includes at least two electrodes, the spacing between said at least two electrodes corresponding to the spacing between said at least two apertures.

7. A medical lead according to claim 6 wherein said inflation lumen means comprises a single inflation lumen in fluid communication with both of said at least two balloons.

8. A medical lead according to claim 1 wherein said lead body is provided with at least first and second elongated lead lumens and wherein said lead body is further provided with a first elongated aperture opening said first lead lumen to the exterior surface of said lead body and a second aperture opening said second lead lumen to the exterior surface of said lead body, said apertures located opposite said expandable means; and
    wherein said medical lead further comprises a first electrode lead slideably mounted within said first lead lumen and a second electrode lead slideably mounted within said second lead lumen, said first and second electrode leads each including at least one electrode.

9. A medical lead according to claim 8 wherein said first aperture is located proximal to said second aperture.

10. A medical lead according to claim 8 wherein said inflation means comprises an inflatable balloon and wherein said lead body comprises an inflation lumen open to the interior of said balloon.

* * * * *